United States Patent [19]

Buck et al.

[11] 3,985,131

[45] Oct. 12, 1976

[54] INFANT AND PEDIATRIC VENTILATOR

[75] Inventors: Keith E. Buck, Alamo; Sotiris Kitrilakis; Thomas C. Robinson, both of Berkeley, all of Calif.

[73] Assignee: Searle Cardio-Pulmonary Systems Inc., Emeryville, Calif.

[22] Filed: Nov. 20, 1974

[21] Appl. No.: 525,309

[52] U.S. Cl. .......................................... 128/145.8
[51] Int. Cl.² ...................................... A61M 16/00
[58] Field of Search ........... 128/145.8, 145.6, 145.5, 128/142, 142.2, 142.3, 145 R, 188, 202, 203, 209, DIG. 17

[56] References Cited
UNITED STATES PATENTS

| | | | |
|---|---|---|---|
| 1,309,686 | 7/1919 | Heidbrink | 128/188 |
| 2,121,311 | 6/1938 | Anderson et al. | 128/145.8 |
| 3,033,195 | 5/1962 | Gilroy et al. | 128/DIG. 17 |
| 3,336,920 | 8/1967 | Thomas | 128/145.8 |
| 3,730,180 | 5/1973 | Davison | 128/145.6 |
| 3,840,006 | 10/1974 | Buck et al. | 128/145.8 |
| 3,898,987 | 8/1975 | Elam | 128/145.8 |
| 3,905,363 | 9/1975 | Dudley | 128/145.8 |

*Primary Examiner*—Robert W. Michell
*Assistant Examiner*—Henry J. Recla
*Attorney, Agent, or Firm*—Lothrop & West

[57] ABSTRACT

A volume ventilating respirator, especially for infant and pediatric use, has a pair of different size volume chambers with means for selecting one or the other for specific use. There is a selector affording a choice of several different ventilating modes including deep breaths at chosen periods or events. The operation is generally automatic with response to patient effort, if desired, and has some responses to manual signals; i.e. deep breath and inspiration. The operation is electric with pneumatic and electronic controls and logic and numerous event indicators and alarms.

4 Claims, 7 Drawing Figures

INFANT AND PEDIATRIC VENTILATOR

Because of the increasing importance of providing health care, there have been developed a number of mechanically operated ventilators for use in assisting patients in breathing. Most of these devices are particularly sized and designed to take care of the breathing requirements of adults. Such devices are not well suited for use in connection with infants, particularly the newly born, even premature, infants, nor are they appropriate for use in pediatric care of young people.

It is therefore an object of the invention to provide a ventilator which is particularly designed for use with infants and which is especially adaptable for use in pediatric care and in fact can be utilized in either instance with benefit.

Another object of the invention is to provide a ventilator which is of an improved construction in general and that will afford a wide variety of selectable operating modes whether for infant and pediatric use or for adult use.

A further object of the invention is in general to provide an improved ventilator.

Other objects together with the foregoing are attained in the embodiments of the invention described in the accompanying description and illustrated in the accompanying drawings, in which.

The present ventilator for volume ventilation of infants and pediatric patients, referred to as a "VVIP", is comparable in many respects to the respirator shown in U.S. Pat. No. 3,840,006, to which reference is particularly made for further information about parts of the respirators that are utilized in both but are not herein described in detail.

For a general understanding of the present arrangement, reference is made primarily to the schematic showing in FIG. 1, which is later supplemented by more detailed information, particularly in connection with FIGS. 2A and 2B. As particularly shown in FIG. 1, atmospheric air is taken in through a conduit 2 and passes through a filter 3 into a power-driven pump 4. This pump is customarily operated by current from commercial power lines and supplies air through a duct 6 at a pressure regulated by a relief valve 7. The duct 6 extends through a sound muffler 8 and to a shuttle valve 9.

It is often the case that the present mechanism is supplied from two sources of air, one driven by commercial power and the other driven by battery power on a standby basis. The second air supply is substantially identical with the one just described and supplies air through a conduit 11 to one end of the shuttle valve 9 with an output pipe 12 between the ends thereof. A ball 13 in the shuttle conduit changes ends to block off whichever source of supply is not momentarily being used. The pipe 12 extends to an air valve 14, which is electrically controlled and opens or closes passage from the pipe 12 into a branch pipe 16.

Also leading to the pipe 16 from an appropriate source of oxygen is an oxygen line 17 extending through a filter 18 and a regulator valve 19 to an oxygen control valve 21 operated electrically and connected to the branch pipe 16. When the valves 14 and 21 are appropriately manipulated, a supply of pure air or pure oxygen or any intermediate admixture thereof can be furnished to a conduit 22 acting as a supply line to a branch 23 connected through an isolation and dump (or vent) valve 24, electrically controlled, to a pediatric volume controller 26 having an appropriate interior displacement volume for pediatric use; for example, a volume of approximately 400 milliliters. The controller 26 is provided with the customary flexible diaphragm 27 with spring return 28 and operates a linear displacement, electrical transducer 29, so that the instantaneous volume within the controller 26 is accurately represented electrically by the output of the transducer 29.

In a comparable fashion, the conduit 22 also leads to a branch 31 in which a check valve 32 is provided, the branch 31 being connected through an isolation and vent valve 33, electrically controlled, to an infant volume controller 34. This is substantially like the controller 26 except that its displacement volume is particularly sized for use by infants and is of the order of 40 milliliters. The construction is substantially as before and is effective to operate a linear displacement, electrical transducer 35 to afford an electrical output comparable to the instantaneous volume displacement of the controller 34. Extending between the branches 23 and 31 is a shunt pump 36 carrying in it an orifice body 37 having an orifice plate 38 therein restricting flow therethrough. Also connected to the conduit 22 is an anti-suffocation valve 41. This is normally closed under interior pressure in the conduit 22, but opens freely when the pressure within the conduit drops to a value below atmospheric pressure.

The conduit 22 continues through an inhalation valve 42 having an electrical control and governing flow into a pipe 43 extending into an inspiratory flow regulation mechanism 44. This includes a chamber 45, flow into which is controlled by a regulating valve 46 operated by a spring-loaded diaphragm 47 on one side connected by a duct 48 to the interior of the chamber 45. The chamber 45 extends through a manually operable throttle valve 49 into a conduit 50 having a shunt tube 51 extending to the other side of the diaphragm 47. The conduit 50 goes into one end of an airway tube 52 in position for use by the patient and having a fitting 53 which is used by the patient in the form of a mask or of an endotracheal tube or the like. The patient can inhale from and exhale into the airway tube 52. An outlet from the airway tube 52 is provided by an exhalation port 54, flow through which is controlled by a balloon-like, expansible exhalation valve 55.

Some of the control structures are operated pneumatically. For that reason there is extended from the output pipe 12 through a filter 56 and through a pressure reducing valve 57 a conduit 58 at its end joined in operating relationship to the exhalation valve 55 through an exhalation pilot valve 61 under electrical control. When the valve 61 is open, pressure in the conduit 58 is effective to enlarge the exhalation valve 55 and to close it, whereas when the valve 61 is closed, the pressure within the valve 55 is released and the valve 55 collapses, permitting the airway 52 to communicate through the opening 54 with the atmosphere.

For some patients it is desired to have some auxiliary equipment. For that reason, the valve 61, instead of discharging directly to the atmosphere when it is in its closed (or venting) position, establishes a connection from the valve 61 through a pipe 62 with a positive exhalation end pressure valve 63. This valve is connected by a duct 64 to the conduit 58, which supplies air under pressure as controlled by a variable needle valve 66 discharging into a chamber 67 open to the atmosphere through a restricted orifice 68. The pressure within the chamber 67 can thus be established at a desired value, so that when the valve 61 is in its closed (or vent) position, that pressure is transmitted through the pipe 62 to the balloon 55 or exhalation valve. This restricts the opening of the valve 55 correspondingly to maintain a positive end expiration pressure within the airway 52.

Pressure within the tube 62 is transmitted through a duct 70 including a restricted orifice 71 and through an electrically controlled transducer valve 72 to a pressure transducer 73. The transducer 73 includes mechanism for translating the pneumatic pressure received into an electrical signal of a comparable value. Various control instrumentalities are thus appropriately signalled to operate the various electrically responsive valves. The transducer valve 72 in one position is joined by a duct 74 to the airway 52, so that airway pressure is communicated to the pressure transducer 73 for signalling purposes. In the other position of the transducer valve 72, the transducer 73 receives its pressure through the restricted orifice 71 from the pipe 62. A gauge 75 is fitted to the duct 74 to indicate the instantaneous pressure therein.

There is a provision for transmitting pressure fluid to the pressure transducer 73, even though the valve 72 may block communication from the orifice 71 although allowing communication with the tube 74. This is accomplished by a shunt tube 76 at one end joined to the duct just below the orifice 71 and at the other end communicating with the transducer 73. Furthermore, in the event certain breathing cycles are to be conducted, particularly during forced inhalation, it is advisable to have a compliant reservoir or balloon. Such a balloon 77 is provided as a compensation bag and is joined by a duct 78 to the duct 70.

With this arrangement, as generally described, the operator can choose either the pediatric volume controller 26 or the infant volume controller 34 by opening or closing the appropriate ones of the valves 24 and 33. Ordinary atmospheric air can be utilized under pressure pumped by commercial current, or pressure air can be derived from an auxiliary source. In addition, oxygen can be introduced into the system in desired proportions. During the functioning of the device, should there be difficulty with the air or oxygen input, the valve 41 opens to afford an immediate atmospheric air supply at atmospheric pressure. In addition, whichever one of the chambers 26 or 34 is utilized, the piping is arranged so that there is no disruption of the responsive controls. The volume of the infant chamber 34 is so small that unrestricted filling is very quick and cannot be properly followed. Consequently, filling is slowed to a reasonable rate. The restriction 38 accomplishes that purpose since the check valve 32 closes during filling and prevents inflow through the branch 31.

Figure 1:
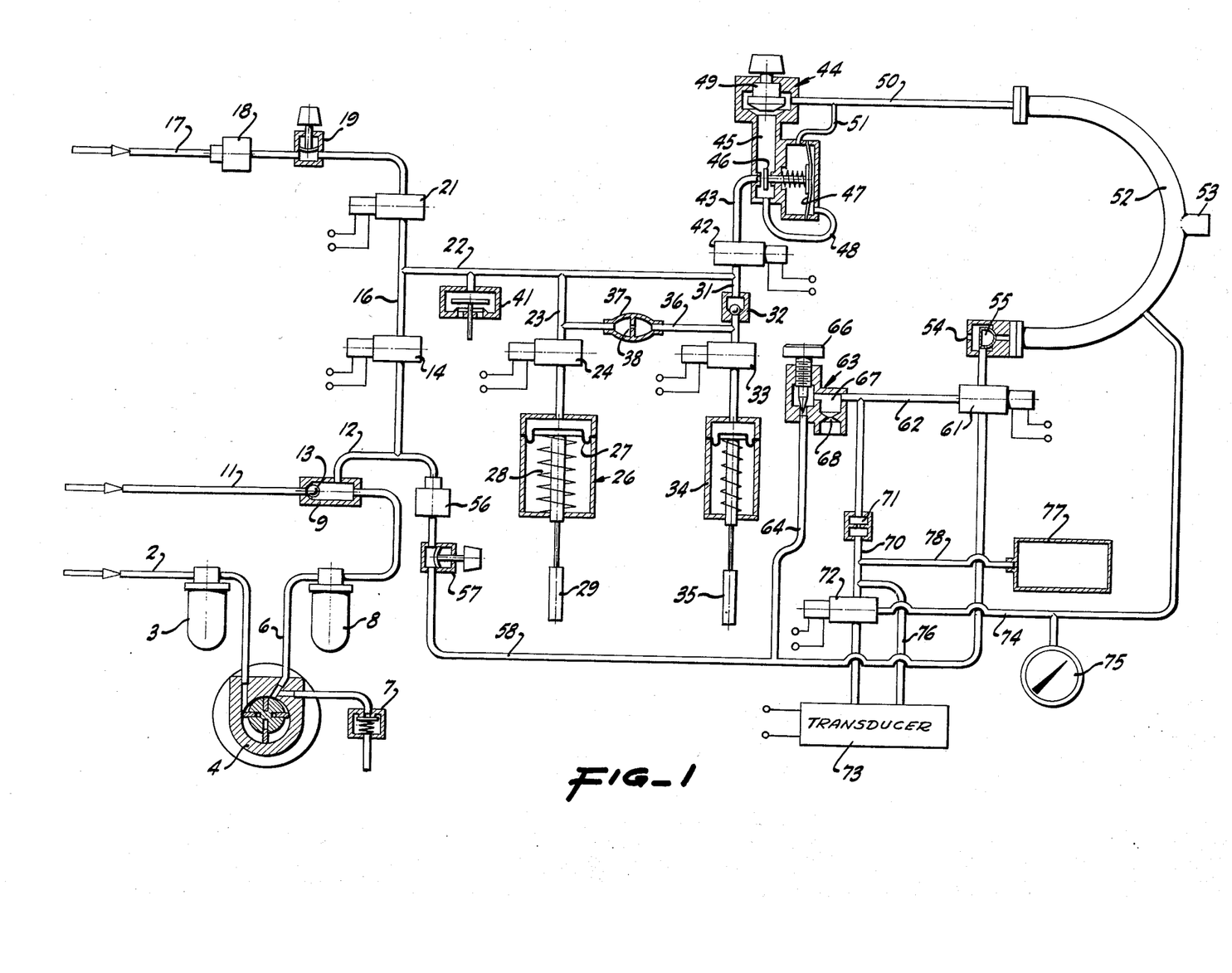
FIG. 1 is a diagrammatic disclosure primarily of the pneumatic circuitry of the present device, many parts being omitted for clarity.

The arrangement as set forth schematically in FIG. 1 is in actual practice inclusive of a good deal of additional circuitry, both pneumatic and electric, and has a number of additional controls, auxiliaries and instrumentalities, although it is primarily an elaboration of the fundamental layout of FIG. 1.

Figure 2A:
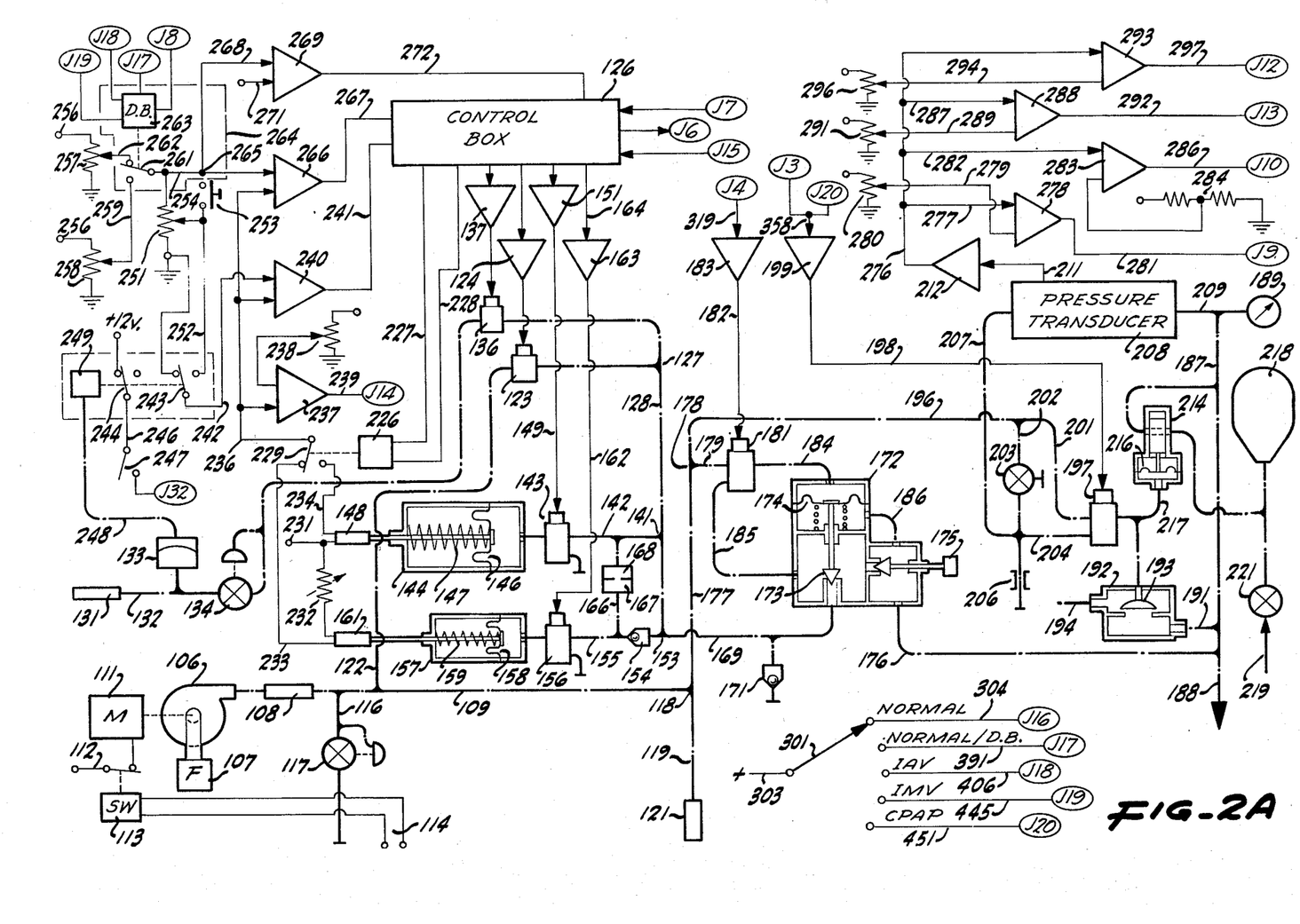
FIG. 2A is a diagram of one portion of the electric and pneumatic connections of the present device.
Figure 2B:
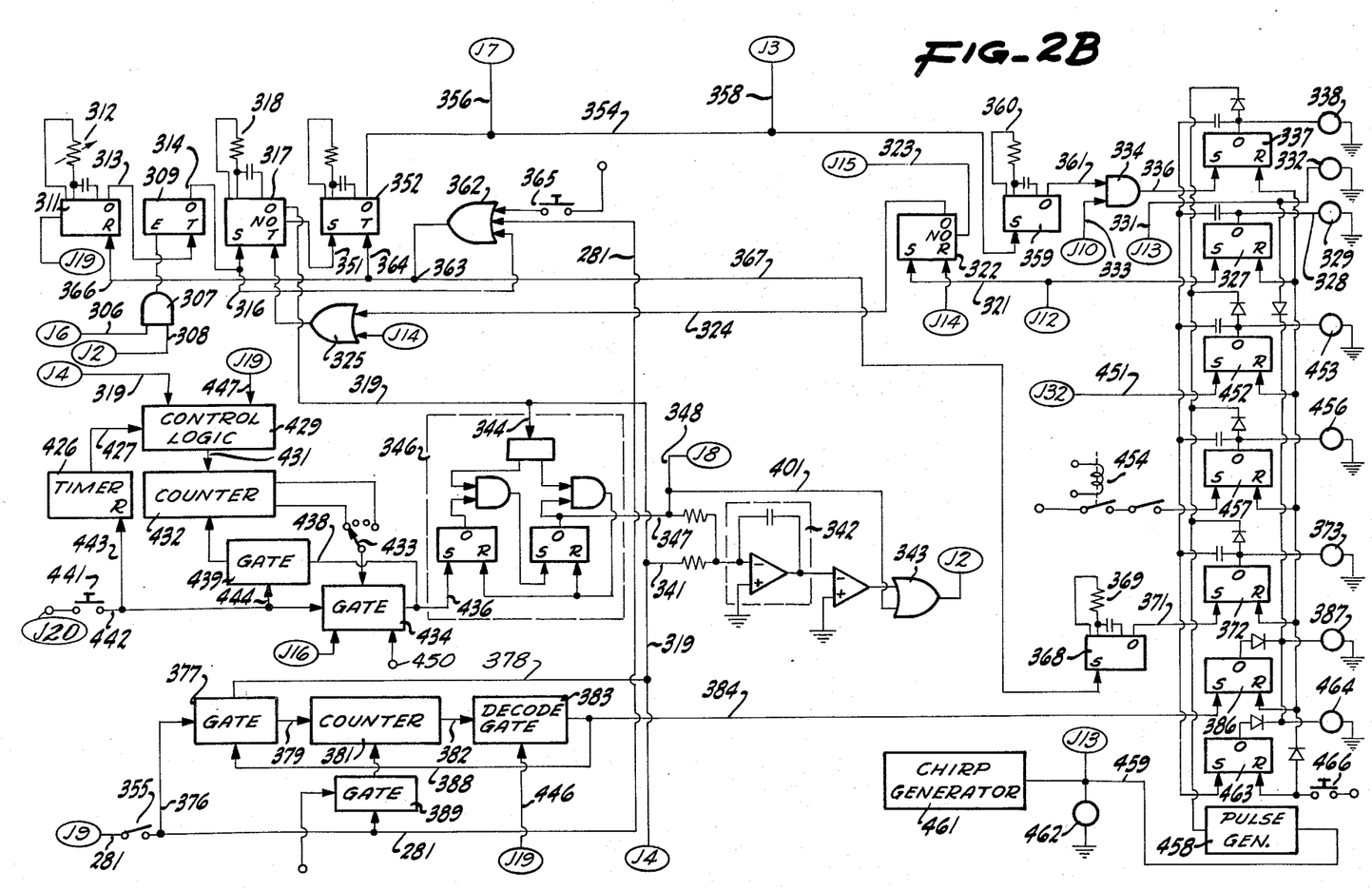
FIG. 2B is a diagram of the remaining part of the pneumatic and electric mechanism of the present device, FIG. 2B completing and matching FIG. 2A when placed to the right thereof.

In the arrangement set forth in FIGS. 2A and 2B, first the portion in FIG. 2A, there is a pump 106 open to the atmosphere through an inlet filter 107 and discharging through a muffler 108 into a main supply line 109. The pump 106 is driven by an electric motor 111 having a power supply 112 thereto stemming from a commercial source under control of a switch relay 113 operated in response to conductors 114 extending to a manual control, not shown. Pressure in the line 109 is controlled by a relief pipe 116 inclusive of a pressure relief valve 117 venting to the atmosphere and capable of maintaining a set pressure in the line 109.

The line 109 extends to a junction point 118, to which is connected an auxiliary supply line 119 from an external, usually battery powered, duplicate source 121 of breathing air. In the event line power is interrupted, the auxiliary supply to the line 119 keeps the junction 118 supplied with air under appropriate pressure.

From the supply line 109 a conduit 122 extends to an air valve 123 which is electrically controlled from an amplifier 124 receiving a control signal from a control box 126. The control box 126 receives impulses from various parts of the structure and supplies signals to other parts of the structure to carry out the chosen program. In this instance, a signal from the box 126 through the amplifier 124 is effective to cause the valve 123 to open and close accordingly. When the valve is closed, there is no flow from the pipe 122, but when the valve is open, there is flow into a junction 127 in a breathing gas line 128.

Sometimes the breathing gas is not simply compressed atmospheric air, but is partly or entirely oxygen. For that reason, there is an oxygen supply 131 discharging into a line 132, the pressure in which is manifest on a pressure switch 133, the control of which is later described.

In the line 132 there is a pressure regulator 134, so that the downstream oxygen is at an appropriate pressure. The line 132 extends to an oxygen control valve 136. This is operated by a signal from the control box 126 acting through an amplifier 137. When the valve 136 is closed, there is no oxygen flow downstream thereof, whereas when the valve is open, oxygen flows to the junction 127. By appropriately opening and closing the valves 123 and 136, there can be a supply of air or of oxygen or of a mixture of the two into the line 128.

In the line 128 there is a first junction point 141 leading to a branch line 142 extending through an isolation and vent valve 143 into a large volume controller 144, this being, in a commercial instance, a volume of approximately 400 milliliters. The volume controller includes a flexible diaphragm piston 146, the movement of which is induced in one direction by a spring 147 in opposition to breathing gas pressure on the other side, and the movement is effective upon a volume transducer 148, which conveniently is a linear electrical potentiometer. In one position of the valve 143, the volume controller 144 is connected to the junction point 141 in the line 128, and in the other position of the valve 143, the line 142 is blocked and the interior of the volume controller 144 is open to the atmosphere. A signal to control these positions of the valve 143 is carried in by a conductor 149 supplied through an amplifier 151 from the control box 126, so that the valve 143 can be opened and closed in accordance with the operation of the structure to be described.

Also in the line 128 is a second junction point 153 leading through a check valve 154 in a line 155 to an isolation and vent valve 156 in turn connected to a small volume controller 157. In a commercial instance this controller has a displacement volume of approximately 40 milliliters. It also has a flexible diaphragm piston 158 urged against incoming gas pressure by a spring 159. It is effective to actuate a transducer 161, conveniently a linear electrical potentiometer, so that the electrical signal available at the potentiometer is directly indicative of the volume in the interior of the controller 157. The valve 156 is like the valve 143 but is controlled through a conductor 162 supplied through an amplifier 163 by a lead 164 extending from the control box 126 and is responsive to appropriate signals thereto for the designed operation of the structure. In addition, the conduits 142 and 155 are cross-connected by a shunt conduit 166 having a chamber 167 with a restricted orifice plate 168 therein, the communication between the lines 142 and 155 being substantially restricted.

In the operation of the device, the valves 143 or 156 (which are utilized alternatively to employ either the large volume controller 144 for pediatric use or to employ the small controller 157 for infant use) take in breathing gas from the line 128 through either of the junctions 141 or 153, whichever is operative due to the position of the corresponding valves 143 and 156. After the respective chamber has been charged when the valves 123 or 136 or both are open, then the effective chamber 144 or 157 discharges its measured contents after both valves 123 and 136 are closed and when the appropriate one of the valves 143 or 156 is open. There is then outflow to the junction point 153 and past that point into a line 169. In the line 169 is an inwardly opening check valve 171 serving as an anti-suffocation valve; that is, if the preceding mechanism in any wise fails to supply breathing gas and so leaves the pressure in the line 169 at a low value, then the valve 171 can automatically open under atmospheric pressure. There is thus available a supply of atmospheric air for breathing.

The line 169 enters into an inspiratory flow rate valve 172 in which there is a valve 173 operated by a spring-pressed diaphragm 174. The inspiratory flow rate valve is internally connected in such a way that there can be a regulated flow of breathing gas at a predetermined rate through a manually adjustable valve 175 into an outlet line 176, all of this being generally in accordance with the disclosure in the above-identified patent. The inspiratory flow rate valve 172 may be subjected to pressure air from the junction 118.

From that junction point there is a conduit 177 extending to another junction point 178, from which goes a line 179 to an inhalation pilot operator valve 181. This is electrically controlled and receives a signal through a conductor 182 extending from an amplifier 183, later described. The valve 181 is connected by a duct 184 to the upper side of the diaphragm 174, whereas a line 185 extends from the valve 181 to the interior chamber surrounding the valve 173. The chamber around the valve 175 and that beneath the diaphragm 174 are interconnected by a duct 186. The line 176 taking the outflow from the inspiratory flow rate valve 172 extends to a patient's airway 187. This is a major part of the structure, and at one end has, as shown in FIG. 1, a fitting 188 connected to the patient, usually by intubation for infants and by a breathing mask in the event of a pediatric patient or an adult. The momentary pressure within the airway 187 is reflected in a pressure gauge 189.

From the line 176 the breathing gas is introduced into the patient's airway 187 under a positive pressure; that is, a pressure above atmospheric, and means are provided for exhausting the patient's airway 187 or reducing or varying the pressure therein in accordance with any one of several programs. As part of the exhaust mechanism, there is connected to the airway by a line 191 an exhalation valve 192. This valve includes an inflatable balloon-like valve closure 193 governing flow between the duct 191 and a vent 194 to the atmosphere. When the balloon valve 193 is inflated, it blocks flow between the members 191 and 194, but when the balloon valve 193 is entirely or partly collapsed, then there is corresponding flow between the elements 191 and 194.

For operating the balloon exhalation valve 193, pressure air is taken from the junction 178 through a line 196 to an exhalation pilot valve 197, itself under electrical control through a conductor 198 extending through an amplifier 199 to a source of appropriate signals, later to be described. The incoming air from the line 196 can follow two paths into the valve 197. There is a line 201 which goes to the valve 197 without interruption, and there is a shunt or parallel line 202 leading through a variable restriction valve 203 to a line 204 not only going to the valve 197 but also having a restricted vent 206 to the atmosphere. With the restricted vent 206 always open, and by adjusting the valve 203, there can be maintained in the line 204 a selected positive end expiration pressure different from the pressure which is in the line 201. The pressure in the line 204 is transmitted through a connector 207 to an airway pressure transducer 208 also having a connector 109 to the airway 187 itself. For various reasons, the effect of the pressures in the lines 207 and 209 on the transducer 208 is made manifest through a conductor 211 extending through an amplifier 212 to control instrumentalities, later to be described.

There is a further connection to the airway 187. In some manners of operation, it is desired to have an additional, compliant volume joined to the airway 187. For that reason, there is provided a control valve 214 moved by a diaphragm 216 receiving control air through a line 217 extending from the valve 197. The valves 193 and 214 open together and close together. The valve 214 is joined between the airway 187 and a flexible chamber 218 or an accumulator having a compliance comparable to that of a patient's lungs. Entering into the balloon also is a secondary gas supply 219 with a manual valve 221 therein, so that if desired a steady supply of external gas separate from the normal breathing gas supply can be afforded the patient when the valve 214 is open. This external supply can be shut off by closing the valve 221 manually.

The control of the various instrumentalities described is generally automatic under various different programs that are manually initially selectable, and the response of appropriate ones of the mechanisms is utilized in carrying out the predetermined one of the selected programs. As shown in FIG. 2A, there is provided a chamber volume selector switch 226 that is remotely controlled, if desired, through conductors 227 and 228 from the control box 126 and is effective to move a switch 229 into either of two positions. In one position, as shown, the switch is connected to the small transducer 161, which receives power from a reference voltage point 231 through a variable calibrating resistor 232 and supplies an analog signal from the volume controller 157 through a conductor 233 to the switch 229. In the other position of that switch, the large volume controller transducer 148, also receiving operating energy from the point 231, supplies an analog signal comparable to the position of the diaphragm 146 through a lead 234 to the other side of the switch 229. When the operator sets the tidal volume, the switch 229 is thereby automatically set for an infant or a pediatric patient.

From the switch 229 the signal from the effective transducer 148 or 161 is supplied through a line 236 to various instrumentalities. One of these is a chamber-empty detector which includes an amplifier 237 connected to the line 236 and also supplied with a settable amount of energy through a variable resistor 238. When the connected transducer is in a position indicating that its respective chamber is empty, a signal is supplied to a lead 239 going to a junction point J14, FIG. 2A and near the upper center of FIG. 2B. In this way, control instrumentalities, later to be described, are made responsive to the chamber-empty signal.

Next connected to the line 236 is an oxygen volume detector inclusive of an amplifier 240 connected by a lead 241 to the control box 126 and joined to the conductor 236 and also connected by a conductor 242 to the blade of a relay switch 243. The switch 243 is ganged with the blade of a switch 244 in a line 246 extending through a control switch 247 to an oxygen alarm connection J32, also appearing at the right portion of FIG. 2B. The switch blades 243 and 244 are moved in response to oxygen pressure at the responsive device 133 effective through a line 248 upon a switch actuator 249.

Normally the blades 243 and 244 are in their right-hand position when there is an adequately pressured oxygen supply, but when the oxygen pressure drops, due to supply failure usually, then the pressure switch 133 moves the blades 243 and 244 into the left-hand position shown. The blade 244 then connects the voltage source to the connector J32 and so to a low oxygen alarm 453, as later described, through a conductor 451 and an alarm control 452.

The effect of the switch 243 is to connect either of two paths to the oxygen volume detector 240. In the left-hand position of the blade as shown, there is a path to the grounded end of a variable resistor 251, whereas in the opposite blade position, there is a straight conductor 252 inclusive of a 100 percent oxygen switch 253. The resistor 251 and the conductor 252 are both joined to a line 254 receiving power from a current supply 256 through a variable resistor 257. This is a tidal volume control. A variable resistor 258 is also connected to the voltage source 256 and is a deep breath volume control. The latter resistor 258 is joined by a conductor 259 to one side of a switch 261, whereas the resistor 257 is joined by a conductor 262 to the other side of the switch 261. This switch joins either of the conductors 259 or 262 to the conductor 254, according to its actuation by a deep breath volume actuator 263, which receives a signal from a connection J8, also appearing near the center of FIG. 2B. The actuator is part of a deep breath control 264 inclusive of an or-gate network, so that the adjustable resistors 257 and 258 can be alternatively connected in circuit or so that the resistor set at the larger value will be connected in circuit.

The line 254 extends through a junction 265 to an air volume detector amplifier 266 also supplied by the line 236. The output of the amplifier 266 is through a lead 267 into the control box 126. This utilizes the signal indicating the size of the air volume cyclically available in subsequently programming the mechanism.

Also from the junction 265 there is a line 268 extending through an amplifier 269 receiving power through a lead 271 and affording an appropriate output signal through a lead 272 to the control box 126.

The signal in the line 272 indicates which of the transducers 148 or 161 is in effect in accordance with the chamber volume selector switch 226, and thus causes the control box 126 through the conductors 149 or 162 to operate the appropriate one of the isolation and vent valves 143 or 156 at appropriate times. The mechanism thus responds automatically to the condition for supplying infant breathing or the condition for supplying pediatric patient breathing. Also, the output of the air volume detector 226 through the lead 267 and the output of the oxygen volume detector amplifier 240 through its lead 241 to the control box 126 are effective to operate the amplifiers 124 and 137 in order to control the air valve 123 and the oxygen valve 136 in the program in accordance with the settings for the use of oxygen alone or atmospheric air alone or the selected admix of the two as arranged by the variable control 251.

As the respirator operates and a patient is ventilated, the pressure within the airway 187 fluctuates. This fluctuation is effective upon the pressure transducer 208. The response of the transducer is transmitted, as described, through the conductor 211 and the amplifier 212 to a conductor 276 having various connections. From the conductor 276 a lead 277 extends to an amplifier 278 also receiving power through a lead 279 from an adjustable potentiometer 280 joined to an appropriate source of voltage, preferably −15 volts. The output of the amplifier 278 goes through a lead 281 to a junction J9, also appearing in the lower left-hand corner of FIG. 2B, and later to be described as a signal serving as a patient effort detector.

The conductor 276 also has a lead 282 to an amplifier 283 receiving an energy supply from a voltage divider 284 and supplying a signal through a lead 286 to a junction J10, also appearing in the upper right-hand portion of FIG. 2B, to supply a signal serving as a low inspiratory pressure detector, later to be described.

Connected also to the conductor 276 is a lead 287 extending to an amplifier 288 supplied with energy through a line 289 from a variable potentiometer 291 connected to a suitable voltage source; for example, +15 volts. The output of the amplifier 288 is carried through a conductor 292 to a junction J13, also appearing in the upper right-hand portion of FIG. 2B as part of a maximum inspiration pressure alarm mechanism. Finally, the conductor 276 extends to an amplifier 293 supplied with energy through a lead 294 from a variable potentiometer 296 connected to the +15 volt source and supplying a signal over a conductor 297 to a junction J12, appearing also in the upper right-hand portion of FIG. 2B, for indicating whether or not a relief valve responsive to inspiration pressure has opened and energized an alarm, as will later be described.

Particularly in accord with the invention, and as shown in the lower right-hand corner of FIG. 2A, there is provided a manually controlled ventilation mode selector switch 301, usually set at the beginning of operation of the respirator. This affords the physician a selection of the type or mode of ventilation cycle to be pursued by the machine automatically. Over a conductor 303 from a suitable source and through the movable switch 301, energy flows into a conductor 304 extending to a junction J16, also appearing in the lower left portion of FIG. 2B. This is for "Normal" operation and is an inhibit signal to preclude certain otherwise available auxiliary functions, which will later be described and set forth in a table appearing near the end hereof.

It can be considered that when the respirator is started the beginning of operations provides air under pressure to the selected one of the volume controllers or chambers 144 or 157, as described, and that such selected chamber expands in interior volume until such time as the related transducer 148 or 161 operates the air volume detector 266 to afford a chamber full signal at a junction J6 from the control box 126. This junction J6 is also found at the upper left-hand corner of FIG. 2B and supplies a signal through a conductor 306 to an and-gate 307. A signal from a terminal J2 (upper left, lower right in FIG. 2B) acts through a conductor 308 on the gate 307, as is later described. With both signals on the and-gate 307, there is a signal to enable an inhalation gate 309.

Timed signals emanate from a normally operating respiration rate timer 311. This has a settable variable control 312 thereon. The periodic signals are available on a conductor 313 leading to the inhalation gate 309. Each signal triggers the gate 309 to supply a signal on a conductor 314 joining a conductor 316 extending to an inhalation control 317. There is a set (say, 5 seconds) time limit device 318 thereon. There is consequently available a signal from the inhalation control 317 on a conductor 319 having branches and extending to a junction J4, appearing also in the upper central portion of FIG. 2A and at the left center of FIG. 2B, later described. From the junction J4 the signal in the conductor 319 extends through the amplifier 183 and the conductor 182 to the inhalation pilot operator 181. In this way, as previously described, the outlet line 176 and the patient's airway 187 are afforded breathing gas under pressure for inhalation.

Should the inspiration pressure get so high as to require relief, that fact is detected by the airway pressure transducer 208 and a corresponding signal appears in the inspiration pressure relief detector conductor 297 at the junction J12 (FIG. 2A) and at the junction J12 (upper right, FIG. 2B) and is found on a conductor 321 extending at one end to a dump valve control 322, from which a signal is carried on a conductor 323 to a junction J15 (also, upper center, FIG. 2A) going to the control box 126 and from there sending signals to move the valves 143 and 156 to vent or "dump" position open to the atmosphere. The signal on the conductor 321 also goes on a lead 324 to an or-gate 325 to terminate the inhalation through the controller 317. Also, the conductor 321 at the other end carries the signal to an inspiration pressure relief alarm control 327 furnishing a signal to a conductor 328 and energizing an alarm light 329.

Should the airway inspiration pressure exceed a predetermined maximum as detected by the transducer 208, then there is a signal on the conductor 292 to the junction J13 (upper right portions of FIGS. 2A and 2B) furnishing a signal over a conductor 331 (FIG. 2B) to an alarm light 332. Furthermore, should the airway inspiration pressure be unduly low, as detected by the airway pressure transducer 208, then a signal appears in the conductor 287 (FIG. 2A) at a junction J10, likewise found at the upper right-hand portion of FIG. 2B, and effective through a conductor 333 and an and-gate 334 to send a signal through a conductor 336 to a low inspiration pressure alarm control 337 for illuminating an alarm light 338. The airway pressure during inhalation is therefore monitored, and alarms are given for any unexpected or abnormal conditions, so that the attendant can be warned.

The conductor 319 has a branch conductor 341 effective through an appropriate integrating network 342, as described in detail in the above-noted patent, to supply a polarized signal to an or-gate 343. The output of the gate 343 is supplied to a junction J2, also found in the upper left-hand corner of FIG. 2B, for supplying the conductor 308, and so through the and-gate 307 enabling the inhalation gate 309, as previously described. Furthermore, there is a branch conductor 344 from the conductor 319 for supplying a signal to a synchronizing logic unit 346, also described in the noted patent. An output signal from the unit 346 is supplied on a conductor 347 and through the integrator 342 to afford a polarized signal to the or-gate 343 and so to the inhalation gate unit 309, as described.

At the end of the inhalation cycle, there is a signal provided over a conductor 351 to the "start" portion of an exhalation control 352. This is provided with a time limit (say, fifteen seconds) control 353. There is a resulting exhalation signal supplied to a lead 354, from which a branch conductor 356 extends to a junction J7, also found in the upper central portion of FIG. 2A. Also extending from the lead 354 (FIG. 2B) is a conductor 358 extending to a junction J3, also in the upper central portion of FIG. 2A, from which the conductor 358 sends the signal through the amplifier 199 to the exhalation pilot operator 197. The exhalation valve 192 is thus opened and the airway 187 is connected to the atmosphere. The conductor or lead 354 (FIG. 2A) also extends to a delay unit 359 having a fixed timer 360 thereon and furnishing a signal through a conductor 361 to the gate 334 for actuating the low inspiration pressure unit 337.

There is provision for initiating inhalation by reason of an effort by the patient to inhale. Such effort by the patient is reflected by a lowering of pressure in the airway 187 during exhalation. This is translated by the transducer 208 (FIG. 2A) into a signal in the conductor 276 which manifests itself at the junction J9 in the conductor 281. As appears in the lower left-hand corner of FIG. 2B, the junction J9 is continued in the conductor 281 through a switch 355 which when closed permits the signal to continue through the conductor 281 and into an or-gate 362 extending to a junction point 363. Like the patient effort signal, the or-gate 362 can also be signalled manually by closure of a switch 365, if the attendant so desires. Further, the conductor 316 carries the signal from the inhalation gate 309 to the or-gate 362. From the point 363, a lead 364 carries whatever signal is put into the or-gate 362 to the terminate section of the exhalation unit 352, which thereupon terminates exhalation.

Branching from the junction 363 is a conductor 366 extending to the reset section of the respiration rate timer 311, so that commencement of inspiration is synchronized. A further branch from the junction 363 is through a conductor 367 into an alarm board 368 having a fixed timer 369 thereon and effective, should the mechanism not respond in the time set, to send a signal through a conductor 371 to a failure to cycle board 372 effective to illuminate a signal light 373 when energized. In this way, inhalation effort by the patient in effect resets the inhalation control 311 and starts a new cycle of inhalation, followed by an exhalation event, as previously described.

The patient's inhalation effort as represented by the signal in the conductor 281 adjacent the switch 355 is also utilized to afford an apnea alarm in the event several inhalation signals are not responded to. Branching from the conductor 281 is a lead 376 extending to an and-gate 377 having an input from a conductor 378 joined to the inhalation valve driver conductor 319. When a normal inhalation signal comes in over the conductor 378 and there is no inhibit signal in the conductor 276, there is an output from the gate 377 over a conductor 379 to a counter 381. After a predetermined number of breath impulses accumulated in the counter, the counter gives an output signal to a conductor 382 and through a decode gate 383 to a conductor 384 leading to an apnea alarm board 386 effective when energized to illuminate an alarm light 387. From the conductor 384, the signal from the decode gate 383 also travels through a lead 388 to inhibit any further input to the gate 377 and counter 381. If, before the counter 381 has made a set count, there is a patient effort signal in the conductor 281, that signal also goes through a gate 389 to reset the counter 381.

It is usually the case under the orders of the physician that the mechanism afford a deep breath to the patient from time to time or upon a chosen event and in some appropriate fashion. If a programmed deep breath mode of operation of cycling is desired (Normal/DB), then the switch arm 301 (FIG. 2A) is moved from its normal mode position in connection with the conductor 304 into its next position connected with a conductor 391, referred to as normal mode with deep breath capability. The conductor 391 goes to a junction J17, also shown at the upper left portion of FIG. 2A, and is effective to energize the deep breath volume switch 263 in the control 264. When energized, this switch moves the switch 261 away from the preset, normal tidal volume control 257 to the preset deep breath volume control 258. While the same volume controller (144 or 157) is continued in use, there is a different volumetric effect in accordance with the setting of the deep breath resistor 258.

A signal to the deep breath volume switch 263 goes through the junctions J8, near the center of FIG. 2B, receiving the signal on the conductor 347 from the synchronizing logic 346. The deep breath thus occurs in synchronism with the timing of a normal breathing or inhalation function but is larger. The signal on the conductor 347 also goes into a conductor 348, which has a shunt branch 401 bypassing the integrator 342 and extending to the or-gate 343 and so to the junction J2 and to the conductor 308 and into the and-gate 307, properly energizing the inhalation gate 309.

The deep breaths may be but usually are not given at each inhalation. They can be given either at preset time intervals or as the end breath of a group of breaths of a selected number; for example, each tenth breath. For this reason, a deep breath controlling network is provided, as shown generally at the left center of FIG. 2B. A timer 426 is always operating when the ventilator is powered and supplies pulses (say, one per second) through a conductor 427 to a control logic board 429. Each inhalation signal in the conductor 319 appearing at the junction J4 (bottom center and left center of FIG. 2B) is also transferred to the control logic board 429, in which the J4 or conductor 319 signal predominates over the timer signal. The inhalation signals go from the logic 429 over a conductor 431 to a counter 432. The counter can be set by a selector arm 433 to accumulate any desired number of signals, say, twenty. The twentieth signal then goes to a gate 434, from which the output signal is sent through a conductor 436 and so through the synchronizing logic 346 to the junction J8 (center of FIG. 2B and top left corner of FIG. 2B), and so actuates the deep breath switch 263. In this way the patient is given a certain number of normal size breaths followed by a larger, deep breath.

Upon occasion, a deep breath can be started manually. A switch 441 in a conductor 442, when manually closed, sends a signal through a branch 443 to reset the timer 426 and also to the counter reset gate 439 through a lead 444. From the conductor 442 the signal goes to the gate 434 and continues as before.

As another choice of ventilation mode, the physician may employ a cycle referred to as intermittent assisted ventilation (IAV). This leaves the patient to conduct much of his breathing himself but nevertheless gives him some assistance in breathing and upon occasion affords him a mandatory deep breath. If that mode is chosen, the switch arm 301 is moved to join a conductor 406 extending to a junction J18, also appearing at the upper left-hand corner of FIG. 2A.

It may be decided to employ a different mode of operation denoted intermittent mandatory ventilation (IMV). In this instance, the switch arm 301 is moved to a conductor 445 going to a junction J19, also appearing at the upper left-hand corner of FIG. 2A, and from which a conductor extends to the deep breath volume switch 263 and has the deep breath effect previously described. Also, the junction J19 appears in three other places in FIG. 2B, one in the lower central portion, another in the left center portion, and the third in the upper left-hand corner. The signal in the upper left-hand corner inhibits the respiration rate timer 311 so that it does not send out timed respiration signals. The junction J19 at the bottom central portion sends a signal over a lead 446 to inhibit the decode gate 383 to prevent transmission of an apnea alarm signal over the conductor 384, while the junction J19 sends an inhibit signal over a conductor 447 to the control logic 429 to prevent transmission of inhalation signals to the counter 432, which then receives signals from the timer 426 and so furnishes a deep breath or mandatory breath signal after a number of timer signals (number of seconds) rather than a number of inhalations. Because of the inhibitions, breathing gas in the IMV mode is furnished from a separate source; for example, through the gas supply 219, the otherwise closed valve 221 being manually opened, and the valves 214 and 192 being open except during the deep or mandatory breaths, when gas is furnished from the regular sources 107 and 131.

As a further distinctive mode of operation, the operator may choose an arrangement in which the patient is supplied through the airway with a continuous positive air pressure (CPAP) and can breathe voluntarily thereunder without mandatorily responding to cycling of the ventilator. If that mode of operation is chosen, then the switch arm 301 is swung into contact with a conductor 451 having a junction J20, which also appears in the lower left portion of FIG. 2B, and is connected by a lead 450 to inhibit the gate 434, so that deep breath signals are not permitted to pass. The junction J20 further appears in the upper right portion of FIG. 2A on the conductor 358 controlling the exhalation valve 192. The signal from the CPAP conductor 451 is an inhibit signal and through the conductor 358 signals the exhalation valve 192 to stay continuously open in this operating mode.

Figure 3:
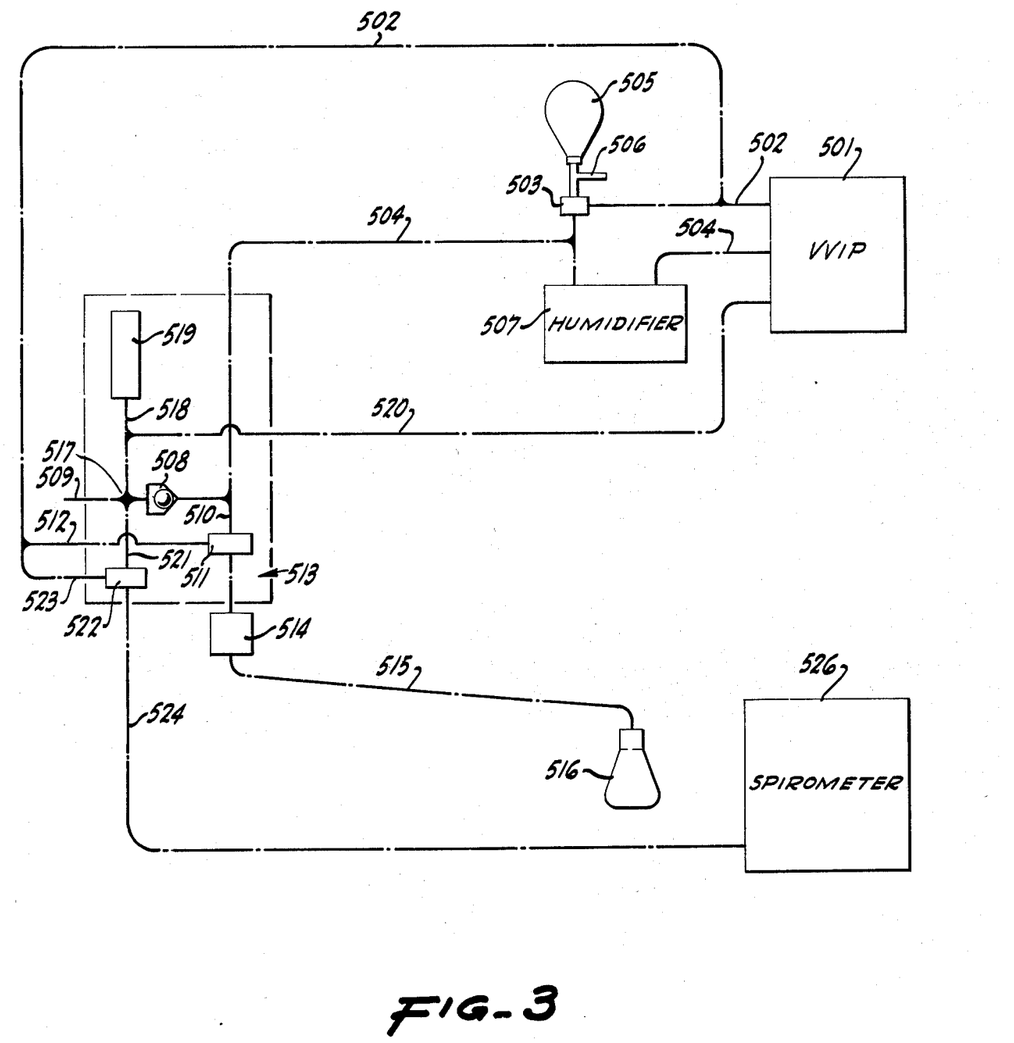
FIG. 3 is a diagram showing a particular manifold or connecting mechanism utilized between the ventilator and the patient.
Figure 4:
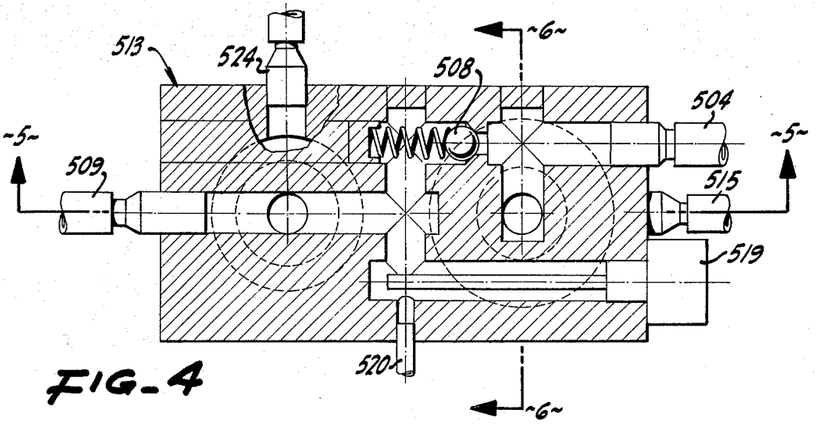
FIG. 4 is a cross-section of a connecting structure utilized with the manifold of FIG. 3, the plane of section being on the line 4—4 of FIG. 5.
Figure 5:
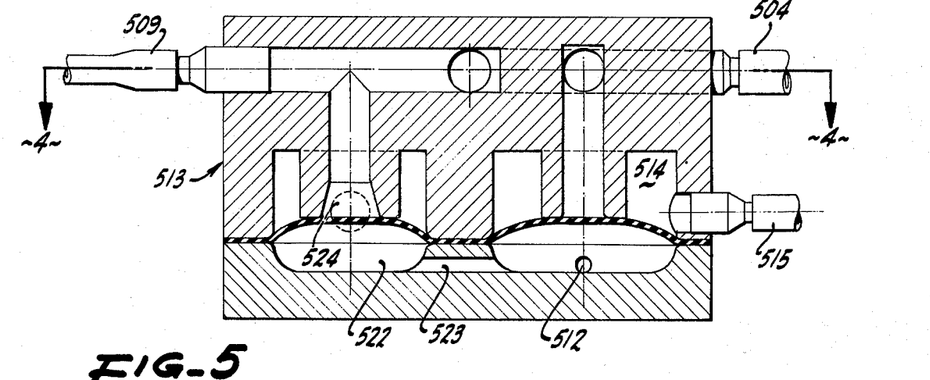
FIG. 5 is a cross-section of the structure of FIG. 4, the plane of section being indicated by the line 5—5 of FIG. 4.
Figure 6:
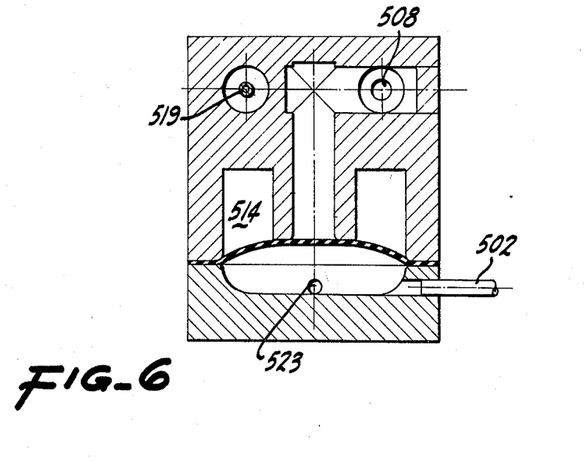
FIG. 6 is a cross-section of the structure of FIG. 4, the plane of section being indicated by the line 6—6 of FIG. 4.

The operation of various valves in the different ventilating modes is in accordance with the approximate table below, in which "Yes" means the valve or control is open or effective, while "No" means the valve or control is closed or blocking. The sign "—" means the valve is not involved in the particular event.

establishing communication between an airway 504 and a compliant reservoir 505 or bag. Upon actuation of the valve 503, communication can be cut off or established between the line 504 and the bag 505. If desired, there can be a normally unused auxiliary gas input line 506 available in some of the selected breathing cycles.

The airway 504 is preferably interrupted in the vicinity of the valve 503 to include a humidifier 507; for example, of the sort shown in the copending application of one of us, Robinson, Ser. No. 403,507, filed Oct. 4, 1973, and entitled "Humidifier". The effect of the humidifier is to increase the moisture content of air flowing through the airway 504.

At its end opposite the VVIP 501, the airway 504 passes through a check valve 508 and extends to a tube 509 or the like for intubation of an infant or for connection to a mask (not shown) in the event the instrument is utilized pediatrically. The airway 504 has a branch 510 extending through a valve 511 actuated by a signal in a branch line 512 joined to the actuating line 502. When closed, the valve 511 blocks the branch 510 but, when open, is effective to permit communication from the branch 510 through the valve 511 into a duct 513. This extends into a water trap 514 having a downwardly sloping gravity drainage tube 515 leading to a collection bottle 516.

The air tube 509 has a junction 517 into which a passage 518 opens. A thermistor temperature probe 519 extends into the passage 518 and is appropriately connected in an electrical circuit (not shown). A pressure duct 520 connects the passage 518 to the respirator 501 to supply airway pressure thereto.

VVIP CONTROL FUNCTION CHART

| | Norm. & D.B. | | IAV | | IMV | | CPAP |
|---|---|---|---|---|---|---|---|
| | Norm. | D.B. | Norm. | Mand. | — | Mand. | Norm. |
| Rate — respiration timer set — 312 | Yes | text | Yes | text | No | | Yes |
| Tidal Volume — controlled — 262 | Yes | text | Yes | No | No | No | Yes |
| Deep Breath Volume — 258 | No | Yes | No | Yes | No | Yes | No |
| Inspiratory Flow — 172 | Yes | Yes | Yes | Yes | No | Yes | Yes |
| PEEP — 203 | Yes | Yes | Yes | Yes | Yes | Yes | Yes |
| O₂ Concentration — 136 | Yes | Yes | Yes | Yes | No | Yes | Yes |
| Patient Effort — 278 | Yes | Yes | Yes | Yes | No | No | Yes |
| Insp. Press. HIGH — 288 | Yes | No | Yes | No | Yes | No | Yes |
| LOW — 283 | Yes | Yes | No | Yes | No | Yes | No |
| Insp. Press. Relief — 293 | Yes | Yes | Yes | Yes | Yes | Yes | Yes |
| Mand. & D.B. Interv. — 433 | — | Yes | — | Yes | — | Yes | — |
| Manual D.B. — 441 | Yes | Yes | Yes | Yes | Yes | Yes | No |
| Manual Inspiratory - 365 | Yes | Yes | Yes | Yes | | Yes | Yes |

Note: Row "Rate — respiration timer set — 312" first column "Norm." = Yes; row "Tidal Volume — controlled — 262" first column "Norm." = Yes; row "Deep Breath Volume — 258" first column = No; row "Inspiratory Flow — 172" first column = Yes; row "PEEP — 203" first column = Yes; row "O₂ Concentration — 136" first column = Yes; row "Patient Effort — 278" first column = Yes; row "Insp. Press. HIGH — 288" first column = Yes; row "LOW — 283" first column = Yes; row "Insp. Press. Relief — 293" first column = Yes; row "Mand. & D.B. Interv. — 433" first column = No; row "Manual D.B. — 441" first column = No; row "Manual Inspiratory - 365" first column = Yes.

The patient fitting or airway attachment referred to before; for example, in connection with the element 53 of FIG. 1 or the element 188 of FIG. 2A, particularly in the case of an infant or pediatric patient, can take on the form illustrated in FIGS. 3, 4, 5 and 6. In this instance, the VVIP is represented (FIG. 3) generally by an enclosure 501 from which extends an actuating air line 502 comparable to the air line 58 of FIG. 1, for example, and extending to an air actuated valve 503

Also from the junction 517 there extends a passage 521 controlled by an exhalation valve 522 having an actuator lead 523 joined to the line 502. The valve 522 controls communication between the passage 521 and an exhalation line 524. This can extend directly to the atmosphere but preferably is connected to a spirometer 526 of the sort shown in the copending application of Kitrilakis, Ser. No. 403,467, filed Oct. 4, 1973, and entitled "Spirometer". There is an atmospheric vent in the spirometer mechanism 526.

In the operation of the device, the airway connector 509 is arranged with the patient in the appropriate way. As the VVIP 501 operates according to the chosen cycle, the inspiration gas flows along the passageway 504, on the way going through the humidifier 507, wherein it picks up additional moisture. If the breathing cycle is arranged to utilize the auxiliary air bag 505, then the valve 503 is appropriately opened by signal in the line 502 from the respirator 501. Furthermore, if an auxiliary gas input is required for the particular breathing cycle, then the fitting 506 is employed. The breathing gas continues through the airway 504 and through the check valve 508 to the junction 517 and to the fitting 509 for the user. The gas passing through the junction 517 has its temperature monitored by the temperature probe 519.

As the moisture laden breathing gas approaches the check valve 508, any extra or surplus moisture therein deposits by gravity and travels through the open valve 511 into the water trap 514 and then flows by gravity down the inclined drain line 515 and is collected in the bottle 516. During exhalation, the valve 511 and the exhalation valve 522 are opened by a signal in the lines 502, 512 and 523. The exhalation gas travels through the line 524 to atmosphere and through the spirometer 526, if utilized. The spirometer advises the attendant of the nature of the exhalation from the patient.

What is claimed is:

1. An infant and pediatric volume ventilator comprising a patient's airway, a first cyclicly operating displacement volume controller having a predetermined volume, means including a first valve for connecting said first controller to said airway, a second cyclicly operating displacement volume controller having a volume larger than said predetermined volume, means including a second valve for connecting said second controller to said airway, means for supplying said volume controllers with breathing gas, means for cross-connecting said connecting means to each other between said valves and said airway, means for selectively closing said first valve and said second valve, a flow restricting device in said cross-connecting means, and means for precluding flow into said second volume controller directly from said supply means.

2. A ventilator as in claim 1 including a downstream opening check valve in said means for connecting said second controller to said airway and disposed downstream of said cross-connecting means.

3. A ventilator as in claim 2 including an inhalation valve in said means for connecting said controllers to said airway.

4. A ventilator as in claim 3 in which said inhalation valve is disposed in said connecting means downstream of said check valve.

* * * * *